United States Patent [19]

Malpass et al.

[11] 3,946,058

[45] Mar. 23, 1976

[54] PROCESS FOR RECOVERING OF DIALKYLALUMINUM HALIDE FROM MIXTURES CONTAINING SOLUBLE ZINC

[75] Inventors: Dennis B. Malpass; George Charles Heilig, both of La Porte; Thomas C. Foley, Pasadena, all of Tex.

[73] Assignee: Texas Alkyls, Inc., Deer Park, Tex.

[22] Filed: June 17, 1974

[21] Appl. No.: 479,693

[52] U.S. Cl................ 260/448 A; 260/429.9
[51] Int. Cl.².......................... C07F 5/06
[58] Field of Search................ 260/448 A

[56] References Cited
UNITED STATES PATENTS

| | | | |
|---|---|---|---|
| 2,996,529 | 8/1961 | Bos | 260/448 A |
| 3,072,697 | 1/1963 | Jenkner | 260/448 A |
| 3,074,986 | 1/1963 | Kaster et al. | 260/448 A |
| 3,124,604 | 3/1964 | Hüther | 260/429.9 |
| 3,475,475 | 10/1969 | Eidt | 260/429.9 |

OTHER PUBLICATIONS

Nesmeyanvo et al., Methods of Elements–Organic Chem. North–Holland Pub. Co. Amsterdam, Vol. 1, p. 400 (1967).
Rochow et al., The Chemistry of Organometallic Compounds, John Wiley & Sons N.Y. p. 105 (1957).

*Primary Examiner*—Helen M. S. Sneed
*Attorney, Agent, or Firm*—Edwin H. Baker

[57] ABSTRACT

A process is disclosed for the recovery of dialkylaluminum halides from a mixture containing dialkylaluminum halides and soluble zinc containing compounds by heating the mixture to pyrolyze the zinc compounds down to acceptable levels and subsequently distilling the alkylaluminum halide from the heated mixture.

7 Claims, No Drawings

PROCESS FOR RECOVERING OF DIALKYLALUMINUM HALIDE FROM MIXTURES CONTAINING SOLUBLE ZINC

This invention relates to a process for recovering dialkylaluminum halide compounds. More praticularly, this invention pertains to a process for recovering dialkylaluminum halides from mixtures containing dialkylaluminum halides and soluble zinc compounds by heating and distilling.

BACKGROUND OF THE INVENTION

U.S. Pat. No. 3,475,475 describes a process for the preparation of dialkyl zinc compounds by the following reaction:

$$Zn + R_3Al + RX \rightarrow R_2Zn + R_2AlX$$

The patent teaches that the dialkyl zinc product of the reaction can be separated by distillation, preferably by vacuum distillation. For example, the patent teaches that diethylzinc, which has a boiling point of 27°C at 10 millimeters Hg pressure, can be distilled from a mixture of diethylzinc and diethylaluminum chloride, as the latter has a boiling point of 91°C at 10 millimeters Hg pressure.

Also, another known process for preparing dialkylzinc compounds involves the following reaction:

$$2 R_3Al + ZnX_2 \rightarrow R_2Zn + 2 R_2AlX$$

The products are also separated by distilling the dialkylzinc compound from the reaction product mixture.

Yields of the dialkylzinc compounds are reported to be good, (around 80 percent or higher) and of high purity, however, the other reaction product, the dialkylaluminum halide is contaminated with soluble zinc. For example, during the preparation of diethylzinc a considerable amount of by-product di-n-butylzinc (bp 201°C) is generated and remains in the still pot after the desired diethylzinc is distilled. The diethylaluminum chloride (bp 114°C) co-distills with di-n-butylzinc, thereby making recovery of diethylaluminum chloride by distillation unsatisfactory.

Other conventional separation techniques, such as preferential complex-formation of one of the compounds are inapplicable.

SUMMARY OF THE INVENTION

Dialkylaluminum halides of high purity are obtained from a mixture of the dialkylaluminum halides and various soluble zinc-containing compounds by heating the mixture strongly to preferentially pyrolyze the zinc-containing compounds and subsequently distilling dialkylaluminum halide of high purity.

Utilizing the process of this invention, 0.6 to 0.7 pounds of dialkylaluminum halide per pound of still pot bottoms are obtained. Dialkylaluminum halide having only about 20–80 p.p.m. zinc are obtainable from the process of this invention. This purity is of the same order of magnitude as commercially available dialkylaluminum halide.

DETAILED DESCRIPTION OF THE INVENTION

Although the applicants do not want to be limited by the particular theory of the reaction mechanism, it is thought that the soluble zinc is present in the mixture primarily as nonrecoverable dialkylzinc compounds. These compounds are thought to decompose upon strong heating according to the equation

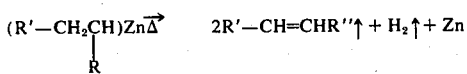

where R' and R" are hydrogen and/or alkyl groups.

Other dialkylzincs are present in small quantities with the reaction product due to impurities in the starting material. $R_3Al$, such as triethylaluminum or tri-n-butylaluminum and alkylzinc halides are suspected to be present. For example, if triethylaluminum were the aluminum alkyl employed in the process of U.S. Pat. No. 3,475,475, tri-n-butylaluminum could constitute 3–6% of the material as an impurity.

The process of this invention particularly is useful for the recovery of dialkylaluminum halides wherein the alkyl group has from 1 to 6 carbon atoms and are either straight or branched chained, preferably ethyl and the halide is a chloride, bromide or iodide, preferably a chloride, or mixtures thereof.

The reaction products of the process of U.S. Pat. No. 3,475,475 and the other prior art process referred to previously thus will be dialkylzinc compound having 1 to 6 carbon atoms and one or two moles of dialkylaluminum halide from 1 to 6 carbon atoms with the halide being a chloride, bromide or iodide, or mixtures thereof.

Contaminating the reaction product mixture are various zinc compounds as previously described.

After the dialkyl zinc reaction product is recovered by distillation, the process of this invention is useful to recover the other reaction product, i.e., dialkylaluminum halide in good yields and high purity.

In the process of this invention the first step of heating the mixture containing the dialkylaluminum halide to preferentially pyrolyze the zinc-containing compounds can be conducted at a temperature range of about 150°–240°C. A more preferred temperature range is about 180°–210°C.

Within these temperature ranges the concentration of zinc-containing compounds can be reduced to an acceptable level of about 200 p.p.m., preferably 20–80 p.p.m. zinc with heating for about 4 to 10 hours. The time of heating will vary depending upon the initial concentration of zinc-containing compounds and the desired reduced level.

The pressure of the process is an important factor in the decomposition rate of the zinc-containing compounds. At a specific temperature, the decomposition rate is increased by reducing the pressure. The maximum degree to which the pressure can be reduced is a function of the selected decomposition temperature and the boiling point of the decomposition mixture at that pressure and the temperature.

For economic reasons, it is desirable to decompose the zinc-containing compounds at the highest practical temperature consistent with the decomposition characteristics of the dialkylaluminum halide and to reduce the pressure to slightly above the point at which the decomposition mixture begins to boil.

Most preferably, the heating step should be run at the highest possible temperature within the recited ranges and at the lowest possible pressure without boiling the mixture containing the dialkylaluminum halide.

Under these preferred conditions, only a slight amount of the mixture is vaporized. However, any vaporized material which has a concentration of dialkylzinc greater than the starting zinc alkyl can be recycled to the primary dialkylzinc purification column and partially recovered as product dialkylzinc.

Stirring of the mixture is not critical, however, the heating step must be done under an inert atmosphere.

The second step of the process of this invention is the recovery of the dialkylaluminum halide from the heated mixture. Preferably, the dialkylaluminum halide is recovered by distillation at reduced pressure between about 10 to 100 mm Hg, however, it can be accomplished at atmospheric pressure.

The second step must also be done under an inert atmosphere.

The following examples serve to illustrate the process of this invention.

EXAMPLE I

The still pot residue of a preparation of diethylzinc according to the process in U.S. Pat. No. 3,475,475 was used as the substrate for this experiment. The material was initially a clear, yellow liquid which contained 19.00% Al, 25.7% Cl and 4.53% Zn. A total of 582.6 g of this material was introduced to a 2 liter flask equipped with a reflux condenser, nagnetic stirring bar, and thermal well. A cold-finger trap was placed in the system to trap volatile gases. The entire system was maintained under at atmospheric pressure of dry nitrogen. The substrate was heated to 160°–190°C for 5 hours during which time a considerable amount of precipitate formed in the flask and a total of 10.7 g of liquid was trapped in the cold-finger. Analysis by vpc showed the trapped material to consist mostly (90%) of butenes. The substrate was re-analyzed after the heating period and found to be 21.03% Al, 27.64% Cl and less than 0.01% Zn. Subsequent vacuum distillation at 60 mm Hg through a 1-foot vacuum-jacketed Vigreaux column afforded two fractions. Analysis of Fraction I (boiling point less than 131°) showed 21.42% Al, 28.38% Cl and 0.0011% Zn (or 109 p.p.m.). Analysis of Fraction II (boiling point 131°–132°C) showed 21.89% Al, 29.21% Cl and 0.0008% Zn (or 83 p.p.m.). The total amount of diethylaluminum chloride obtained was 375.6 g or a yield of 0.64 pounds of diethylaluminum chloride per pound of substrate initially charged.

EXAMPLE II

The still pot residue of a preparation of diethylzinc according to the process of U.S. Pat. No. 3,475,475 is used as substrate for this experiment. In this example, however, the dialkylaluminum halide is a mixture consisting of about 80% diethylaluminum chloride and about 20% diethylaluminum iodide. After heating strongly for 6 hours the soluble zinc containing compounds are completely decomposed and the product is then distilled under reduced pressure.

EXAMPLE III

This experiment was conducted to determine the rate of decomposition of the zinc-containing compounds in the substrate of Example I. Thus, a total of 119.8 g of substrate (analysis above) was charged to a flask equipped with a thermal well, magnetic stirring bar, reflux condenser and dip tube. The mixture was heated rapidly to 167° ± 3°C and samples taken periodically by pressuring the samples through the dip tube into a flask immersed in dry ice. The samples were analyzed immediately. The results of these analyses are compiled in the following table.

TABLE

| Pyrolysis Time (Minutes) | Analytical Data | | |
|---|---|---|---|
| | Wt.% Al | Wt.% Cl | Wt.% Zn |
| 0 | 19.00 | 25.70 | 4.53 |
| 30 | 19.20 | 25.81 | 3.77 |
| 90 | 19.38 | 26.07 | 3.02 |
| 150 | 19.77 | 26.49 | 2.40 |
| 240 | 20.19 | 26.79 | 1.76 |
| 300 | 20.25 | 26.69 | 1.32 |

From this data, it was calculated that the zinc-containing compounds in the mixture have a half life of about 2.9 hours at 167° ± 3°C.

EXAMPLE IV

The still pot residue of a preparation of di-n-propylzinc employing the alkylation of zinc chloride by tri-n-propylaluminum is used as substrate for this experiment. Substrate is charged to the same equipment employed in Example I, and the material is heated to 175°–185°C. for 10 hours. Again, during the heating period a large amount of precipitate forms. The mixture is submitted to vacuum distillation and di-n-propylaluminum chloride is collected.

EXAMPLE V

This experiment was conducted to determine the effect of pressure on the rate of decomposition of diethylzinc (DEZ) in diethylaluminum chloride (DEAC). A synthetic solution of 9 wt.% DEZ and 91 Wt.% DEAC was prepared to approximate a typical still pot residue composition from the preparation of DEZ according to the process delineated in U.S. Pat. No. 3,475,475.

For each run, 35 lbs. of the above solution was charged to a 5 gallon stainless steel reactor. The operating pressure was first established and then the material was brought up from ambient to operating temperature. The progress of the decomposition was followed by sampling the reaction mixture at 1 hour intervals from the point at which the reaction mixture reached operating temperature to the termination of the run 6 hours later. The following table shows the run temperatures, pressures and pseudo first order rate constants ($k_R$) for the six runs of this experiment;

TABLE

| Run | Temp. °C. | Pressure TORR | $k_r$ hr$^{-1}$ | Relative $k_r$ |
|---|---|---|---|---|
| A | 132 | 250 | −0.027 | 1.42 |
| B | 132 | 760 | −0.019 | 1.00 |
| C | 167 | 760 | −0.273 | 14.37 |
| D | 167 | 1,551 | −0.231 | 12.16 |
| E | 150 | 760 | −0.079 | 4.16 |
| F | 150 | 1,551 | −0.065 | 3.42 |

It can be seen from the above data that for a specific temperature, the pseudo first order rate constant increases with reduction in pressure.

EXAMPLE VI

The purpose of this experiment was to determine if DEAC, low in soluble zinc content, can be recovered from DEZ still bottoms by the process of this invention. Therefore, 46 lbs. of DEZ still bottoms (obtained by the process of U.S. Pat. No. 3,475,475) which contained 0.18% soluble zinc, was charged to a 5 gallon stainless steel reactor. The soluble zinc pyrolysis step was carried out at 132°C and 250 TORR by the procedure of Example IV. The following data was obtained:

| Decomposition Time (Hrs.) | Analytical Data | | |
|---|---|---|---|
| | Al Wt.% | Cl Wt.% | Zn PPM |
| 0 | 21.27 | 24.29 | 1,798 |
| 1 | 21.41 | 24.38 | 206 |
| 2 | 21.27 | 24.22 | 96 |
| 3 | 21.36 | 24.23 | 72 |
| 4 | 21.31 | 24.21 | 23 |
| 5 | 21.09 | 24.13 | 21 |

On completion of the pyrolysis step, the pyrolyzed still pot residue was placed under 80 TORR and a flash distillation was carried out at 135°C. 35 lbs. of clear DEAC with the following analysis was recovered: Al— 21.61 wt.%, Cl— 25.88 wt.%, Zn— 19 p.p.m. and Cl/Al— 0.910.

It is claimed:

1. A process for the recovery of dialkylaluminum halides having from 1 to 6 carbon atoms from a mixture of the alkylaluminum halide and soluble zinc-containing compounds which comprises heating the mixture in an inert atmosphere at a temperature of about 150°–240°C. for a period of time sufficient to reduce the concentration to 200 ppm or lower zinc, and subsequently distilling the alkylaluminum halide from the mixture in an inert atmosphere.

2. The process of claim 1 in which the alkyl group is methyl, ethyl, n-propyl or n-butyl.

3. The process of claim 1 in which the halide is chloride, bromide, iodide or mixtures thereof.

4. The process of claim 1 in which the heating step is carried out at a pressure slightly above the vapor pressure of the mixture.

5. The process of claim 1 wherein the heating is done at reduced pressure above the vapor pressure of the mixture for a time sufficient to reduce the concentration of the zinc to about 20–80 ppm and the distilling of the dialkylaluminum halide is done at reduced pressure.

6. The process of claim 5 wherein the dialkylaluminum halide is diethylaluminum chloride.

7. The process of claim 5 wherein the dialkylaluminum halide is a mixture of diethylaluminum chloride and diethylaluminum iodide containing 0.01 to 20 wt.% diethylaluminum iodide.

* * * * *